(12) United States Patent
Cooper

(10) Patent No.: US 7,140,740 B1
(45) Date of Patent: Nov. 28, 2006

(54) VEHICLE SIDE-VIEW MIRROR WATER REMOVAL ARRANGEMENT

(76) Inventor: Joseph Richard Cooper, 504 Russell Hill Est., Sugar Valley, GA (US) 30746

( * ) Notice: Subject to any disclaimer, the term of this patent is extended or adjusted under 35 U.S.C. 154(b) by 0 days.

(21) Appl. No.: 11/240,953

(22) Filed: Sep. 30, 2005

(51) Int. Cl.
*B60R 1/06* (2006.01)
*G02B 5/08* (2006.01)

(52) U.S. Cl. ........................................... 359/509
(58) Field of Classification Search ................ 359/509
See application file for complete search history.

(56) References Cited

U.S. PATENT DOCUMENTS

| | | | |
|---|---|---|---|
| 3,288,378 A * | 11/1966 | Dobson | 239/547 |
| 3,656,691 A * | 4/1972 | Norstrand | 239/284.2 |
| 4,044,953 A * | 8/1977 | Vogel | 239/229 |
| 4,505,001 A * | 3/1985 | Fasolino | 15/250.02 |
| 4,561,732 A * | 12/1985 | Japes | 359/509 |
| 4,611,761 A * | 9/1986 | Pollard | 239/284.1 |
| 4,898,453 A * | 2/1990 | Hohenecker | 359/509 |
| 6,290,361 B1 * | 9/2001 | Berzin | 359/507 |
| 2005/0180152 A1 * | 8/2005 | Haag | 362/494 |

FOREIGN PATENT DOCUMENTS

DE  3212007  * 10/1983  ............ 15/250.003

* cited by examiner

*Primary Examiner*—Mark A. Robinson
*Assistant Examiner*—Scott Stephens
(74) *Attorney, Agent, or Firm*—Eric R. Katz

(57) ABSTRACT

A vehicle side-view mirror water removal arrangement is easily retrofitted to vehicles having an existing source of compressed air and a side-view mirror with a reflective surface. The arrangement includes a valve having an input port connected to the existing source of compressed air and an output port, the valve being movable between open and closed positions to control the flow of compressed air from the existing source of compressed air to the output port of the valve. A conduit's proximal end is connected to the output port of the valve with its distal end located at the side-view mirror for conducting the compressed air from the output port of the valve to the side-view mirror. A fastener fastens the distal end of the conduit to the side-view mirror so that the compressed air flows down the reflective surface of the side-view mirror, a nozzle at the distal end being provided to spread the compressed air substantially over an entire width of the side-view mirror to clear any water adhering to the reflective surface of the mirror.

10 Claims, 4 Drawing Sheets

VEHICLE SIDE-VIEW MIRROR WATER REMOVAL ARRANGEMENT

BACKGROUND OF THE INVENTION

1. Field of the Invention

The present invention generally relates to an arrangement for clearing a vehicle side-view mirror of water adhering to the reflective surface of the side-view mirror, and more particularly, to such an arrangement for use on large vehicles such as trucks, buses and other vehicles in which the mirror is separated from the vehicle body and/or positioned remotely from the driver side of the vehicle and out of reach from the driver.

2. Background of the Invention

On large trucks, side-view mirrors provide the only effective means for enabling the driver of the vehicle to observe traffic and related conditions on both sides and to the rear of the vehicle. While systems are readily available for removing rain water from vehicle windshields, side-view mirrors generally are not provided with such systems.

Unfortunately, because such side view mirrors are mounted in positions outwardly of the side view windows of the vehicle, they are also in a position exposed to the accumulation of snow, ice, mud, rain water and other foreign material on the reflecting surfaces. This is particularly true during inclement weather, the very time when use of the mirror becomes even more critical because during wet and rainy conditions, rain water adheres to the side-view mirror making it difficult to see the reflected image. Since large vehicles such as trucks do not have rear-view mirrors in the cab, the driver must rely solely on the side-view mirrors to see what is behind them and to make lane changes and the like. As a result, this lack of visibility results in safety concerns when driving in wet conditions.

While periodic cleaning of the mirrors ensures good visibility under normal driving conditions, it is difficult if not impossible for a driver to constantly keep the surface of the side-view mirrors clean during unfavorable driving conditions and when the vehicle is in motion, because the side-view mirrors of a large vehicle like a truck are separated from the vehicle body or positioned remotely from the driver side of the vehicle making it difficult for the driver to reach the mirror while driving to clean off any rain water adhering to the mirror surface. Also, these mirrors are high off of the ground, making it difficult to clean them when stopped at a truck stop. Moreover, during wet and rainy weather, the mirrors need to be cleaned quite often so stopping to repeatedly clean these mirrors is not really an option and cuts into profits due to the increased travel time.

There are arrangements for cleaning side-view mirrors such as disclosed by U.S. Pat. No. 4,928,580 to Mcintyre et al. which relates to an automobile windscreen cleaning device using high a velocity flow of air. As best seen in FIG. 1, a turbine 32 produces a high volume of high velocity air that is conducted by hoses 54, 55 to side-view mirrors 14, 16 respectively, to emit air upwardly over the surfaces of the mirrors to effect a cleaning and clearing action. However, this arrangement cannot be easily retro-fitted to existing vehicle configurations, requires the addition of a turbine not normally found on passenger vehicles and is operationally inefficient for use to clear a side-view mirror of adhering rain water since the flow of air is upward over the surfaces of the mirror and counter to the pull of gravity.

Other known arrangements are disclosed by U.S. Pat. Nos. 4,134,612 and 4,196,930 respectively to Nelson and Busche, which relate to vehicle mirror cleaning devices which use air flow deflections to direct a stream of air across the face of the mirror and provide a cleaning effect but these arrangements are generally ineffective since the force of the stream of air is limited by the vehicle's speed. U.S. Pat. Nos. 1,932,798 2,849,760 4.538,85 4,928,580, disclose vehicle windscreens or side-view mirror cleaning devices using wiper arrangements and are highlighted as an indication of the general state of the art.

Accordingly, the need has arisen for a means by which side-view mirrors on trucks and other large vehicles can be easily and effectively cleared of rain water during inclement weather in a quick, easy and effective manner without the need for the driver to stop repeatedly to manually wipe the mirrors, thus improving driving safety for all on the road.

SUMMARY OF THE INVENTION

Accordingly, it is an object of the present invention to provide a new and useful arrangement for clearing the reflective surface of a side-view mirror during inclement weather which overcomes the deficiencies of the prior art.

Another object of the present invention is to provide a vehicle side-view mirror water removal arrangement which is easily retrofitted to large vehicles without the need for expensive adaptations and the like.

Yet another object of the present invention is to provide a vehicle side-view mirror water removal arrangement that can be used while driving the vehicle without the need for the driver to move from the driver's seat.

Still another object of the present invention is to provide a vehicle side-view mirror water removal arrangement that for issues a downwardly directed sheet of compressed air from the top portion of the side-view mirror substantially over the entire reflective surface of the side-view mirror to blow off any water adhering to the reflective surface.

One particular advantageous feature of the present invention is that it provides a vehicle side-view mirror rain water removal arrangement that is operable manually as needed or automatically with the operation of the windshield wipers.

Yet another advantageous feature of the present invention is that it can be used in connection with the existing air brake and/or air suspension arrangement normally found on large vehicles such as trucks and buses thereby eliminating the need for and the expense of adding an auxiliary high pressure source to the vehicle.

The present invention thus relates to a vehicle side-view mirror water removal arrangement that is easily retrofitted to vehicles having an existing source of compressed air and a side-view mirror with a reflective surface. The arrangement includes a valve for controlling the flow of compressed air from the existing source of compressed air to a conduit connected to an output port of the valve to the side-view mirror. A fastener, such as hot glue or the like, fastens the distal end of the conduit at the top of the side-view mirror so that the compressed air flows down the reflective surface of the side-view mirror. A nozzle at the distal end is provided to spread the compressed air substantially downward over the reflective surface of the side-view mirror to clear any water adhering to the reflective surface of the mirror when the arrangement is switched on from the driver's seat within the cab of the vehicle.

These and other objects, advantages, and features of the present invention are achieved by a vehicle side-view mirror water removal arrangement for a vehicle having an existing source of compressed air and a side-view mirror with a reflective surface, the arrangement comprising: a valve having an input port connected to the existing source of compressed air and an output port, the valve being movable between open and closed positions to control the flow of compressed air from the existing source of compressed air to the output port of the valve; a conduit having a proximal end connected to the output port of the valve and a distal end located at the side-view mirror for conducting the compressed air from the output port of the valve to the side-view mirror; a fastener for fastening the distal end of the conduit at the side-view mirror so that the compressed air flows down the reflective surface of the side-view mirror; a nozzle for spreading the compressed air issued from the distal end of the conduit substantially over an entire width of the side-view mirror; and a switching mechanism for opening and closing the valve to provide a downwardly directed blast of compressed air over the reflective surface of the side-view mirror to clear water adhering to the reflective surface.

DETAILED DESCRIPTION OF THE PREFERED EMBODIMENT(S)

Figure 1:
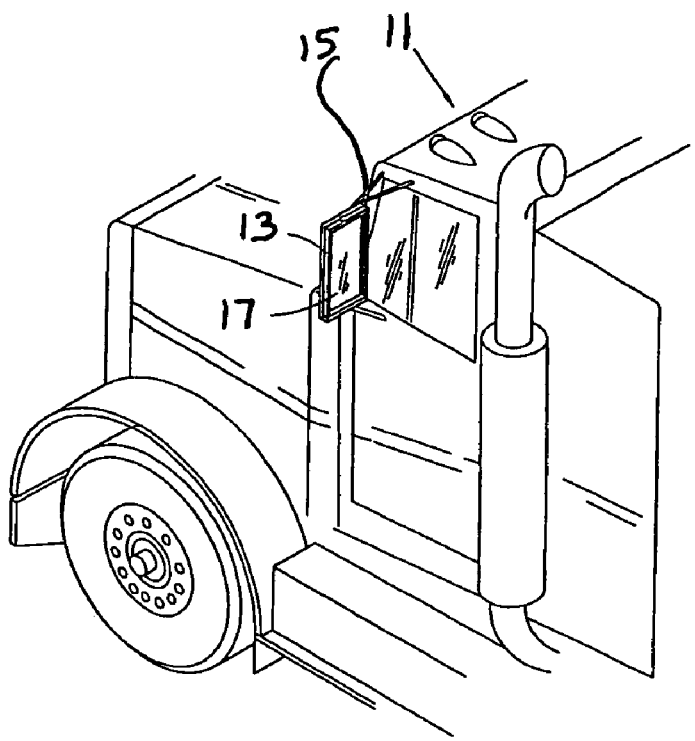
FIG. 1 is a perspective view of a large vehicle having a side-view mirror separate from the vehicle body and located on the driver side of the vehicle in accordance with the prior art.
Figure 2:
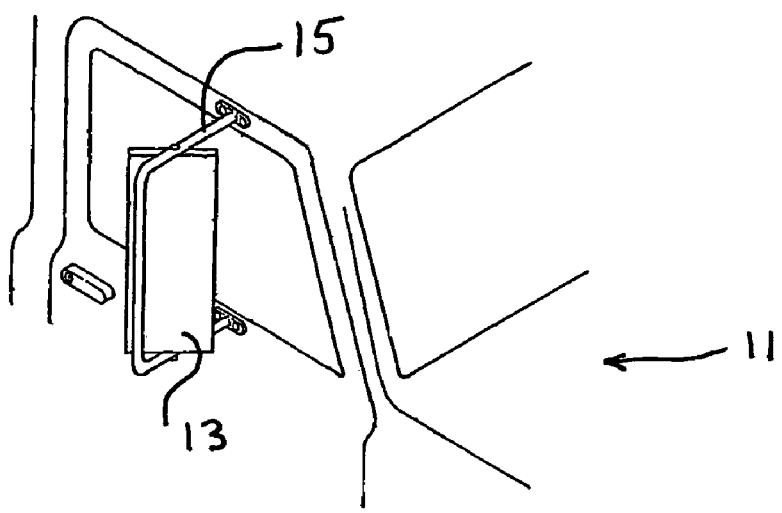
FIG. 2 is a perspective view of a large vehicle having a side-view mirror separated from the vehicle and located on the passenger side of the vehicle in accordance with the prior art.

Referring to FIGS. 1 and 2, a large vehicle, generally indicated at 11, such as a truck, wherein such large vehicles are typically provided with air brakes and/or an air suspension system requiring an on-board source of compressed air (not shown). The large vehicle 11 is shown having side view mirrors 13 mounted in positions outwardly of the side view windows of the vehicle 11 on supports 15. As a result of this arrangement, the side view mirrors 13 are in a position exposed to the accumulation of rain water, wet road water misting and other foreign material on the reflecting surfaces 17.

This is particularly true during inclement weather, the very time when use of the mirror 13 becomes even more critical because during wet and rainy conditions, rain water and/or water mist from wet road surfaces adhere to the side-view mirrors 13 making it difficult to see the reflected image. Since a large vehicle 11 such as a truck does not have a rear-view mirror in the cab, the driver must rely solely on the side-view mirrors 13 to see what is behind them and to make lane changes and the like. As a result, this lack of visibility results in safety concerns when driving in wet conditions.

Periodic cleaning of the side-view mirrors 13 ensures good visibility under normal driving conditions, but it is difficult if not impossible for a driver to constantly keep the reflective surfaces 17 of both of the side-view mirrors 13 clean during inclement weather when the vehicle is in motion, because the side-view mirror 13 on the passenger side of the large vehicle 11 is positioned remotely from and outside of the reach of the driver's position making it difficult for the driver to reach the mirror 13 while driving to clean off any rain water adhering to the mirror surface 17 with a rag or the like.

Figure 3:
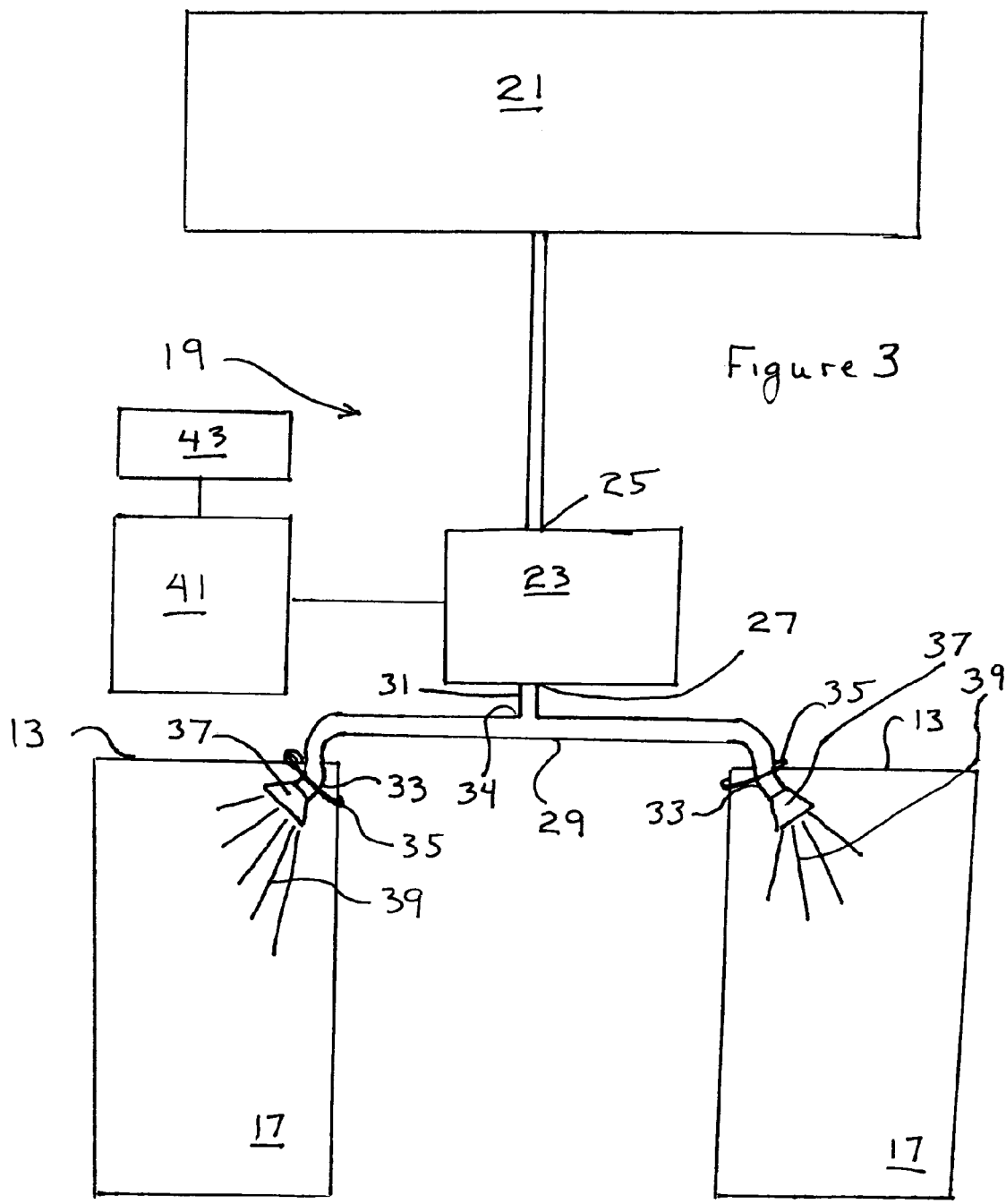
FIG. 3 is a block diagram illustrating the components of one embodiment of the arrangement of the present invention.

Referring to FIG. 3, a block diagram illustrates the basic components of a vehicle side-view mirror water removal arrangement, generally indicate at 19. The arrangement 19 is adapted use with a vehicle having an existing, on-board source of compressed air 21. A valve 23 connects the arrangement 19 to the existing, on-board source of compressed 21. The valve 23 has an input port 25 connected to the existing source of compressed air 21 and an output port 27, the valve 23 being movable between open and closed positions to control the flow of compressed air from the existing source of compressed air 21 to the output port 27 of the valve 23.

A conduit 29 has a proximal end 31 connected to the output port 27 of the valve 23 and a distal end 33 located at the side-view mirror 13. The conduit is preferably made of a flexible material and by way of example may be comprised of plastic or elastomeric materials, noting however, that metallic materials are also within the scope of permissible conduit materials. In the embodiment shown in FIG. 3, a t-connector 34, by way of example, is employed so that the conduit 29 conducts the compressed air from the output port 27 of the valve 23 to both of the side-view mirrors 13 of the vehicle although it is understood that the present invention is applicable to a single side-view mirror arrangement too.

A fastener 35 is also provided for fastening the distal end 33 of the conduit 29 at the side-view mirror 13 so that a blast of compressed air 39 issued from the distal end 33 of the conduit 29 is directed at and flows down over the reflective surface 17 of the side-view mirror. The fastener 35 comprises for example glue as well as other known mechanical fasteners such as ties and the like, however, glue is preferred because it permits the accurate positioning of the distal end 33 of the conduit 29 at the side-view mirror 13.

A nozzle 37 is provided at the distal end 33 of the conduit 29 for spreading the blast 39 of compressed air issued from the distal end 33 of the conduit 29 is fanned out over the reflective surface 17 of the side-view mirror 13. The inventor has found that a malleable ring made of metal and crimped onto the distal end 33 of the conduit provides an effective and inexpensive way of forming the nozzle so that it is not blown off with the blast 39 of compressed air issued from the distal end 33 of the conduit 29.

The arrangement 19 also include a switching mechanism 41 for opening and closing the valve 23 to provide the blast 39 of compressed air from the compressed air source 21 to the distal ends 33 of the conduit 29. As more fully discussed below, the switching mechanism comprises a toggle switch manually operated by the driver to provide the blast of air or automatically operated when the windshield wipers of the vehicle are turned on or a combination of both manual and automatic.

Figure 4:
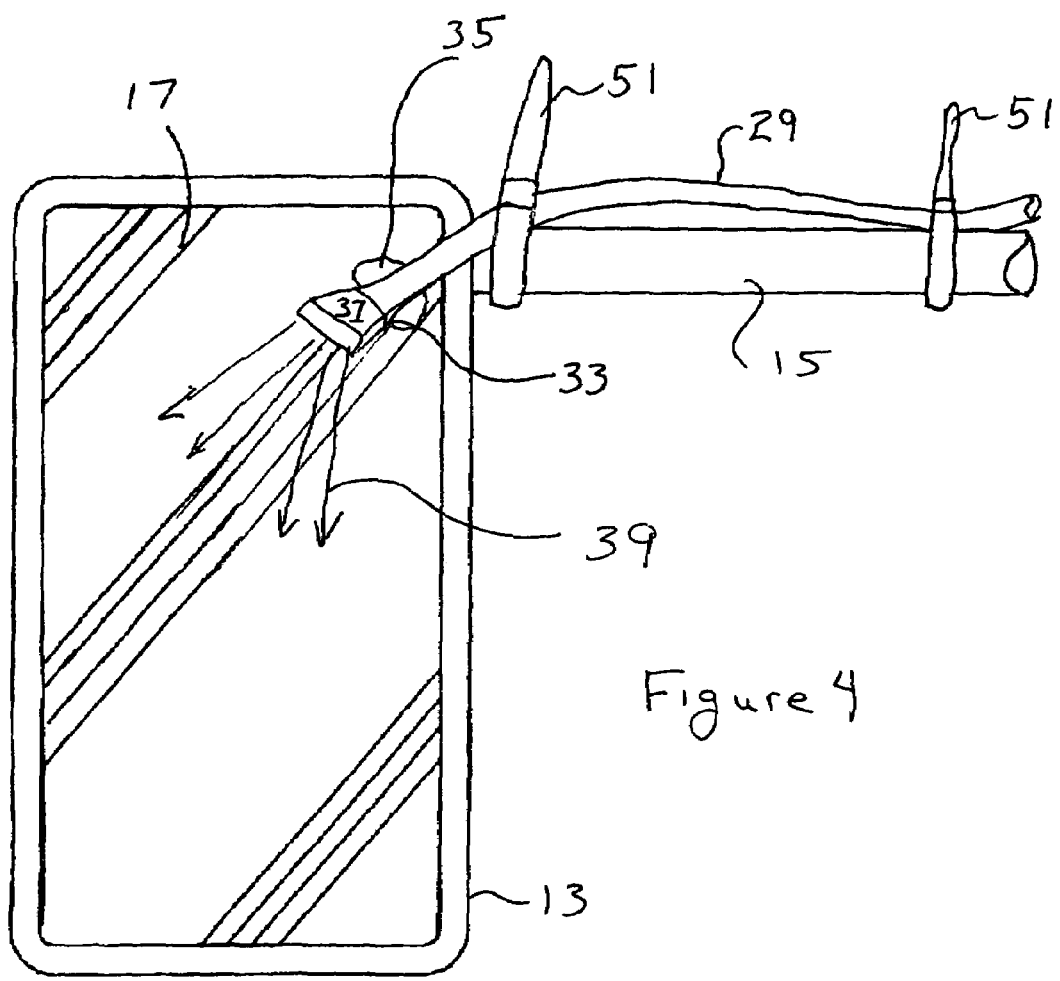
FIG. 4 is a planar view of the arrangement of the present invention at the side-view mirror of the vehicle.

Referring to FIG. 4, a detailed view of one embodiment an arrangement for attaching the distal end 33 of the conduit 29 at the side-view mirror 13 is illustrated. In this embodiment the conduit 29 is secured along the mirror support 15 using, for example, ties 51 or the like, although any suitable fastening arrangement can used, and the distal end 33 of the conduit 29 is secured at the reflective surface 17 of the mirror 13 using glue 35. The use of glue 35 permits the precise positioning of the nozzle 37 at the reflective surface 17, preferably at a top portion of the side-view mirror 13 so that the blast 39 of compressed air is directed generally downward and at a substantial portion of the surface 17 of the mirror 13. In cooperation with gravity, the blast 39 of air blows off water adhering to the reflective surface. The nozzle 37 facilitates a fanning out of the blast 39 of compressed air to form a sheet of high velocity fluid flowing over the surface 17 and forcing adhering water to the edges of the mirror 13 where it is carried away by the air through which the vehicle is moving.

Figure 5:
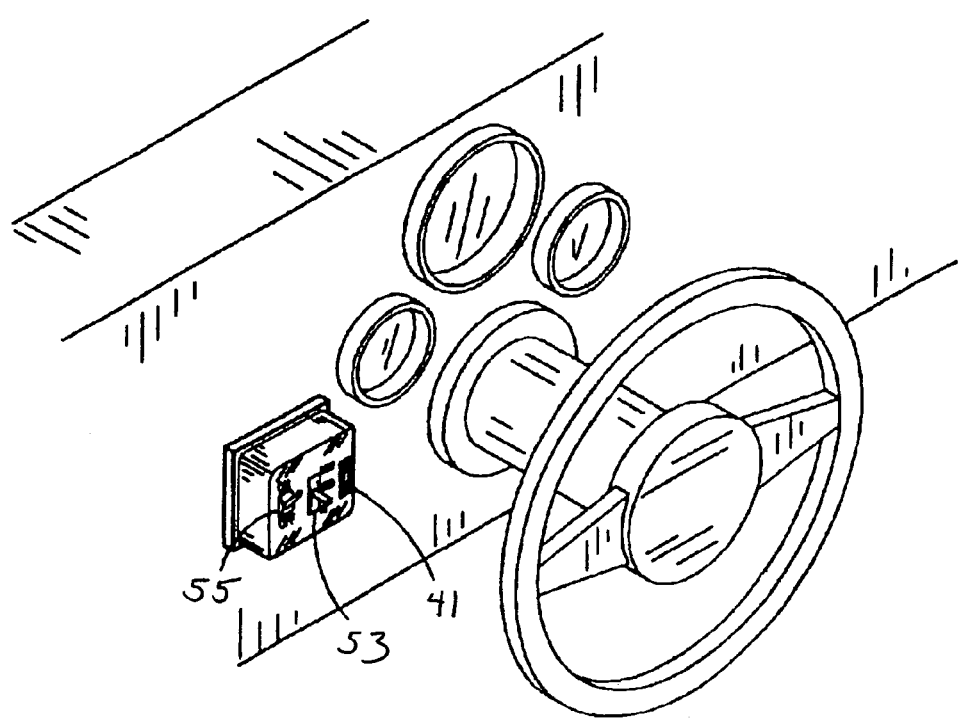
FIG. 5 is a perspective view of various embodiments of the switching mechanism of the present invention.

With particular reference to FIG. 5, the switching mechanism 41 is located in the cab of the vehicle 11 within easy reach from the driver's position. The switching mechanism 41 comprises a manual switch, such as a toggle switch 53 operated manually by the driver or it can be made to operate automatically by connecting the switching mechanism 41 to the windshield wiper switching mechanism 55 so that a blast of air to the side-view mirrors is provided periodically to the side-view mirrors, such as, for example, each time the windshield wipers cycle across the windshield. In addition, the switching mechanism can comprise a combination of both the manual toggle switch 53 and the automatic arrangement connected to the windshield wiper mechanism so that if an immediate clearing of the side-view mirror is necessary, the driver can toggle the toggle switch and send a blast of air to the side-view mirrors as much as needed.

Although the present invention has been described in terms of specific exemplary embodiments, it will be appreciated that various modifications and alterations might be made by those skilled in the art without departing from the spirit and scope of the invention as specified in the following claims.

What is claimed is:

1. A vehicle side-view mirror water removal arrangement for a vehicle having an existing source of compressed air and a side-view mirror with a reflective surface, the arrangement comprising:
    a valve having an input port connected to the existing source of compressed air and an output port, the valve being movable between open and closed positions to control a flow of compressed air from the existing source of compressed air to the output port of the valve;
    a conduit having a proximal end connected to the output port of the valve and a distal end located at the side-view mirror for conducting the compressed air from the output port of the valve to the side-view mirror;
    a fastener for fastening the distal end of the conduit to the reflective surface of the side-view mirror so that the compressed air flows down the reflective surface of the side-view mirror;
    a nozzle on the distal end of the conduit and precisely positioned on the reflective surface of the mirror for spreading the compressed air issued from the distal end of the conduit substantially over an entire width of the side-view mirror; and
    a switching mechanism for opening and closing the valve to provide a blast of compressed air at the reflective surface of the side-view mirror to clear water adhering to the reflective surface.

2. An arrangement according to claim 1, wherein the vehicle has a side-view mirror on each side of the vehicle and the valve has a pair of output ports each respectively connected to a conduit for conducting the compressed air to one of the side-view mirrors on each side of the vehicle.

3. An arrangement according to claim 1, wherein the switching mechanism is located within easy reach of a driver location of the vehicle.

4. An arrangement according to claim 3, wherein the switching mechanism is manually operated by a driver of the vehicle.

5. An arrangement according to claim 4, wherein the vehicle has windshield wipers that turn on and off and wherein the switching mechanism is automatically operated to periodically provide blasts of air to the side-view mirror while the wipers are turned on.

6. An arrangement according to claim 1, wherein the conduit comprises flexible tubing.

7. An arrangement according to claim 6, wherein the nozzle is a malleable ring crimped onto the distal end of the flexible tubing.

8. An arrangement according to claim 1, wherein the fastener fastens the distal end of the conduit at a top end of the mirror.

9. An arrangement according to claim 1, wherein the fastener is glue.

10. An arrangement according to claim 1, wherein the distal end of the conduit is positioned at a top portion of the side-view mirror for issuing a generally downwardly directed sheet of compressed air from the top portion of the side-view mirror over substantially the entire reflective surface of the side-view mirror to blow off any water adhering to the reflective surface.

* * * * *